United States Patent [19]
Gut Boucher

[11] 4,207,286
[45] Jun. 10, 1980

[54] SEEDED GAS PLASMA STERILIZATION METHOD

[75] Inventor: Raymond M. Gut Boucher, New York, N.Y.

[73] Assignee: Biophysics Research & Consulting Corporation, New York, N.Y.

[21] Appl. No.: 887,374

[22] Filed: Mar. 16, 1978

[51] Int. Cl.² .................. A61L 1/00; A61L 5/00; A61L 13/00; A61L 13/02
[52] U.S. Cl. ...................... 422/21; 422/22; 422/23; 422/28; 422/33; 422/36; 422/37
[58] Field of Search .............. 21/54 R, 58, 102 R; 422/22, 23, 28, 33, 37, 36, 21

[56] References Cited

U.S. PATENT DOCUMENTS

| | | | |
|---|---|---|---|
| 3,383,163 | 5/1968 | Menashi | 21/54 R |
| 3,490,500 | 1/1970 | Brumfield et al. | 422/21 X |
| 3,551,090 | 12/1970 | Brumfield et al. | 422/21 |
| 3,600,126 | 8/1971 | Hellund | 422/23 |
| 3,701,628 | 10/1972 | Ashman et al. | 21/54 R |
| 3,753,651 | 8/1973 | Boucher | 21/54 R |
| 3,876,373 | 4/1975 | Glyptis | 21/54 R |
| 3,948,601 | 4/1976 | Fraser et al. | 21/54 R |
| 3,968,248 | 7/1976 | Boucher | 424/333 |

*Primary Examiner*—Barry S. Richman
*Attorney, Agent, or Firm*—Shoemaker and Mattare, Ltd.

[57] ABSTRACT

A method to sterilize the surfaces of objects placed in a continuous flow of a low temperature, low pressure gas plasma, containing small amounts of aromatic, heterocyclic and saturated or unsaturated acyclic aldehydes alone or mixtures thereof. Said gas plasma is a partially ionized gas composed of ions, electrons and neutral species. It is created by electromagnetic discharges at subatmospheric pressure in the 1 to 10,000 Megahertz range, and corresponds to a minimum average spatial energy density of 0.001 watts per cubic centimeter.

The gas plasma may also contain other vaporized cidal agents. Contrary to most sterilant gases, the method is safe, allows quick handling of heat sensitive items, does not corrode equipment and does not leave toxic residues.

12 Claims, 5 Drawing Figures

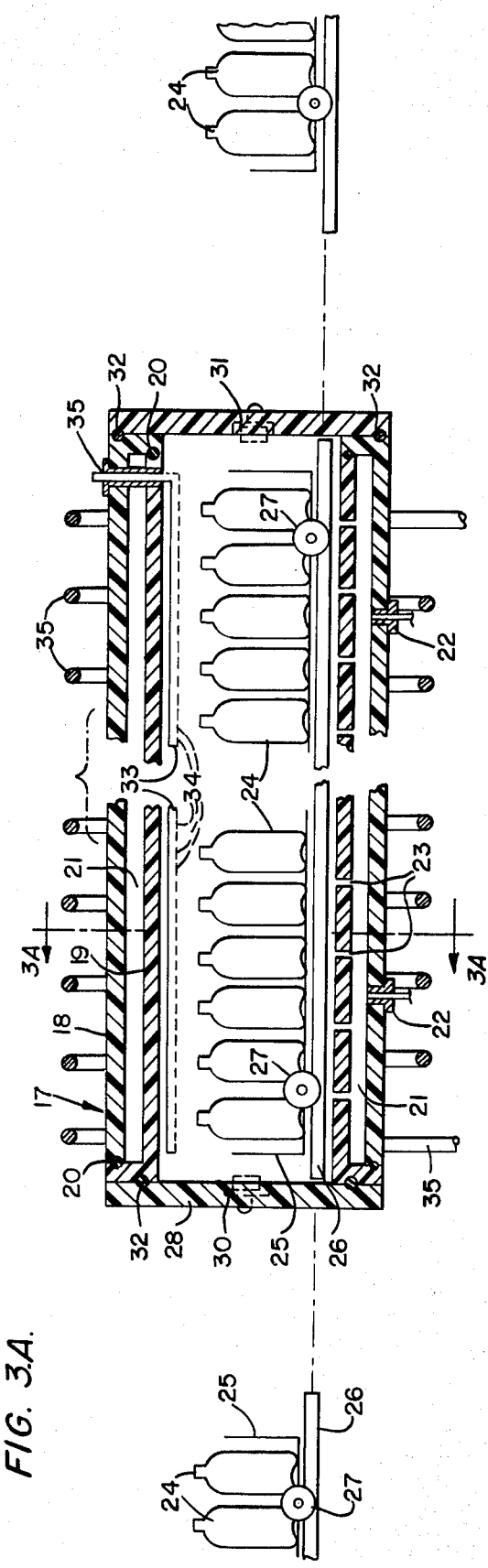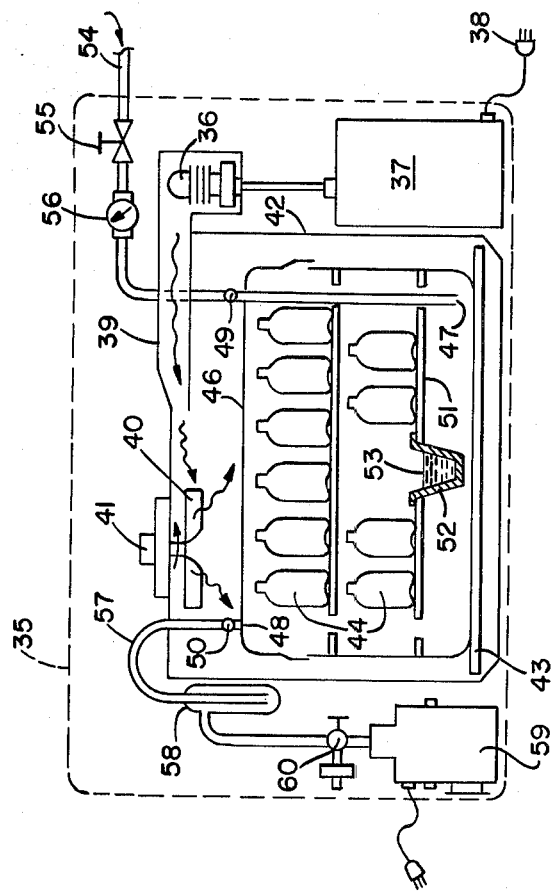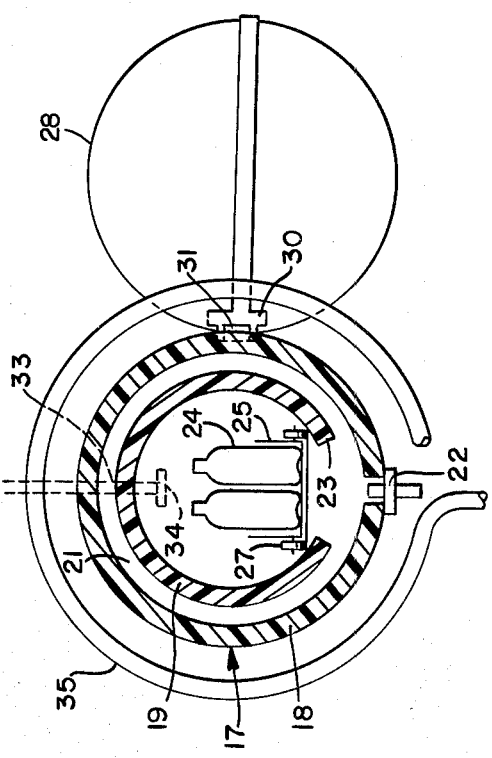

SEEDED GAS PLASMA STERILIZATION METHOD

BACKGROUND OF THE INVENTION

1. Field of the Invention

This invention relates to gaseous sterilization which is the treatment of objects or materials with a chemical in the gaseous or vapor state to destroy all microorganisms with which they have contaminated. The need for such a method of sterilization has developed from the use of many items that cannot be subjected to heat, radiation, or liquid chemical sterilization.

2. Description of the Prior Art

In practice, only two gases or vapors have been commercially used on a large scale for surface sterilizing purposes; they are formaldehyde vapors and ethylene oxides gas.

Formaldehyde vapors have been used as a fumigant for many decades in the Hospital, agricultural and industrial fields. The limitations of this technique are numerous. To kill tough aerobic and anaerobic bacterial spores at room temperature, one needs at least a 24 hour contact time with a vapor having at least 70% relative humidity. This type of vapor is extremely corrosive and the fumes are very irritating. It is also very difficult to maintain a high level of formaldehyde gas since $CH_2O$ is stable in high concentrations only at temperature above 80° C. in humid air. At ordinary room temperatures formaldehyde gas quickly polymerizes and it dissolves readily in the presence of water. Thus gaseous sterilization with formaldehyde has been regarded as a misnomer because introduction of formaldehyde gas into a closed space serves mainly as a mechanism for distributing either moisture films in which formaldehyde is dissolved or solid formaldehyde polymers over all available surfaces within the enclosed space. This indeed explains why very inconsistant and sometimes contradictory results have been reported in hospital disinfection, patient rooms, bedding, etc., or agricultural applications such as eggs and hatcheries sanitizing. Formaldehyde vapor has very weak penetrating ability and, if used in an atmosphere with traces of hydrochloric acid, it can quickly produce (70° F., 40% RH) Bis-(chloromethyl)-ether which is a carcinogenic agent.

To minimize the abovementioned drawbacks in Hospital applications, a new approach was recently developed which combines the use of subatmospheric steam and formaldehyde gas at 80° C. in autoclaves. This method is said to kill most sporulated microorganisms at the concentration normally encountered in Hospital practice while decreasing the aldehydes residue on instruments. It requires a time exposure of two hours with a formalin concentration of 8 gr. per cubic foot of autoclave. However, despite the long contact time and the relatively high temperature, the method would not satisfy today's stringent requirements of the sporicidal AOAC test in this country.

In short, formaldehyde vapors, besides their toxicity and irritating characteristics are difficult to handle at room temperatures and they do not provide a fast and reliable method to satisfactorily handle most of the Hospital and industrial applications.

This may explain why in the past two decades ethylene oxide (ETO) has become the most popular method to gas sterilize both in Hospitals and industry. In a recent survey entitled "Use of Ethylene Oxide as a Sterilant in Medical Facilities" (NIOSH, August, 1977), Dr. Z. R. Glaser mentioned that at least 6,500 hospitals use ETO sterilizers. Since most average hospitals (i.e., 200–300 beds) use at least two units, it is estimated that at least 20,000 hospital ETO sterilizers are in use. This corresponds to an investment of the order of 120 million dollars with replacements and sales of new units growing at a fast rate.

While at the beginning ETO seemed an ideal technique to replace formaldehyde fumigants, very serious limitations from the toxicity view point recently attracted the attention of Health Authorities.

In the previously mentioned NIOSH report, it is stated that

"The acute toxic effects of ETO in man and animals include acute respiratory and eye irritation, skin sensitization, vomiting and diarrhea. Known chronic effects consist of respiratory irritation and secondary respiratory infection, anemia, and altered behavior.

"The observations of (a) heritable alterations in at least 13 different lower biological species following exposure to ETO, (b) alterations in the structure of the genetic material in somatic cells of the rat, and (c) covalent chemical bonding between ETO and DNA support the conclusion that continuous occupational exposure to significant concentrations of ETO may induce an increase in the frequency of mutations in human populations At present, however, a substantive basis for quantitative evaluation of the genetic risk to exposed human populations does not exist . . . However, the alkylating and mutagenic properties of ETO are sufficient bases for concern about its potential carcinogenicity. Neither animal nor human data are available on which to assess the potential teratogenicity of ETO . . . Although this review is limited to ETO, concern is also expressed for hazards from such hydration and reaction products of ETO as ethylene glycol and ethylene chlorohydrin, the latter a teratogen to some lower biological species."

The average time needed to sterilize medical instruments in an ETO unit is 180 minutes at 30° C., but it has to be followed by a long de-aeration period. For instance, the de-aeration time for medical devices is comprised between 2 and 8 hours in a de-aerator machine, but it oscillates between 1 and 8 days at room temperature. On rubber gloves, the residues can burn the hands; on tubes carrying blood, they will damage red blood cells and cause hemolysis. Endotracheal tubes which are not properly aerated can cause tracheitis or tissue necrosis.

Besides the risks due to the toxicity of ETO residues, other accidents have been reported due to the explosive characteristics of pure ETO. As little as 3% ethylene oxide vapor in air will support combustion and will have explosive violence if confined. To solve this problem, various gases such as $CO_2$ or fluorinated hydrocarbons have been mixed with ETO in some commercial formulations.

In short, ETO sterilization grew tremendously not because it was an ideal solution, but rather because there seemed to be no alternative gas sterilant method which was capable of as fast a sporicidal action without any drawbacks from the toxicological or environmental view point.

The object of the present invention is to provide an alternative to ETO sterilization with the advantages of faster sporicidal action, no de-aeration period, no toxic residue, and no explosion risk. Moreover, this invention will provide a more economical approach from the running and investment cost view point when comparing the volume of material treated per unit of time.

When speaking hereafter of sterilization, it always refers to sporicidal action against *B. subtilis* ATCC 19659 and *Clostridrium sporogenes* ATCC 3584 because they are the resistant microorganisms used in the fumigant-sterilant test according to the legal requirements of the AOAC (Official Method of Analysis of the Association of Official Analytical Chemists, 12th ed., Nov. 1975). It is indeed to be understood that the destruction of these two species of spores according to the official procedure means automatically the destruction of other less resistant microorgaisms such as Mycobacteria, non lipid and small viruses, lipid and medium size viruses and vegetative bacteria.

DESCRIPTION OF THE INVENTION

To better understand the cidal mechanism of a low temperature gas plasma, one must first consider the physical structure of a highly resistant spore. As can be seen in FIG. 1, the typical bacteria spore is first surrounded by an exosporium which is a loose sac peculiar to some spores species. From the outside to the inside one finds, successively, (a) multi-layered coats containing disulphide (—S—S—) rich proteins, (b) the thick cortex layer which contains the polymer murein (or peptidoglycan), (c) the plasma membrane, and (d) the core or spore protoplast.

The first line of resistance to exogenous agents consists of the proteinaceous outer coats which contain keratin like proteins. As it is well-known, the stability of keratin structures is due to frequent primary valence cross links (disulphide bonds) and secondary valence cross links (hydrogen bonds) between neighboring polypeptide chains. Keratin like proteins are typically strong, insoluble in aqueous salt solutions or in diluted acid and basic solutions. They are also resistant to proteolytic enzymes and hydrolysis. In other words, the layered outer coats are rather inert and play a predominant role in protecting the spore against exogenous agents.

Several attempts have been made in the past to learn more about the exact composition of the protective outer coats. V. Vinter (1961) and Kadota et al (1965) were the first to demonstrate the presence of disulphide rich proteins with a physical structure resembling keratins. Then G. W. Gould et al (1970) showed that reagents which break disulphide bonds by oxidation alter the coat sufficiently to allow lysozyme-like enzymes or hydrogen peroxide to penetrate through the altered coat and reach the peptidoglycan cortex region. These authors also showed the presence in the outer coats of an alkali soluble protein which in vitro tended to form fibrils. The alkali soluble layer could only be removed after spores mechanical rupture or treatment with a reagent like mercaptoethanol which breaks disulphide bonds. It was speculated that the disulphide rich layer held the alkali soluble layer onto the spore in some manner (physical admixture or disulphide bridges for instance).

The importance of the reactions taking place in the outer layers has been also stressed by several authors trying to better understand the cidal mechanisms of dialdehydes on spores (*B. subtilis*) or gram-negative bacteria (*E. coli*). For instance, A. D. Russell et al (1971) speculated that the difference in cidal activity between acid and alkaline glutaraldehyde solutions at room temperature could be explained by the alkaline effect on outer layers since electrophoretic mobilities measurements showed a faster blockage of alkaline aldehydes on the surface layers of *B. subtilis*. These authors assumed an amino-aldehyde interaction. In the case of several gram-negative bacteria (*E. coli, S. marcescens, K. aerogenes*, etc.) the same authors found a red coloration of the outer layer of the bacteria in the presence of alkaline glutaraldehyde, while no coloration was observed with acid glutaraldehyde. These authors again speculated about protein-dialdehyde interactions on the outer layer under alkaline conditions. In other experiments, Russell and Munton (1972) explained the action of dialdehydes on cytoplasmic enzymes by a "sealing" of outer layers through protein-aldehydes interaction.

In short, outer layers seem to play an important role in cidal action through physical or chemical modifications which affect the diffusion of cidal molecules, excited atoms or radicals inside the microorganism protoplast.

To alter the multilayered outer coats and thus allow further penetration and possible interactions in the critical cortex or protoplast regions, one much choose a very active agent. It is, therefore, the main object of the present invention to use an ionized gas plasma as the ideal vehicle to provide reactive atoms, free radicals, and molecules which will drastically alter the protective layers of bacteria, fungi, and spores.

It is a further object of the present invention to show that the seeding of low temperature oxidizing gas plasmas with aldehydes will considerably increase the destruction of both sporulated and non-sporulated microorganisms.

It is another object of this invention to show that the addition of small amounts of aldehyde vapors into an ionized low temperature non-oxidizing gas plasma can also, in some cases, accelerate the destruction of sporulated and non-sporulated microorganisms.

To aid in the understanding of this invention, the following is a brief review of the various physical or chemical mechanisms which play a cidal role and explain the improved biocidal efficacy of the present invention.

In short, the present invention consists of exposing the objects to be decontaminated to a continuous flow of gas plasma seeded with small amounts of aromatic, heterocyclic, saturated or unsaturated aldehydes. The gas plasma is a partially ionized gas composed of ions, electrons, and neutral species. Such a state of matter can be produced through the action of either very high temperatures or strong electric or magnetic fields. The present invention deals with ionized gas produced by gaseous electric discharges. In an electrical discharge, free electrons gain energy from the imposed electric field and lose this energy through collisions with neutral gas molecules. The energy transfer process leads to the formation of a variety of highly reactive products including metastable atoms, free radicals, and ions.

For instance, in an oxidizing plasma, some of the active species are the atomic oxygen and $^1\Delta g$ molecular oxygen which is also called "singlet oxygen." A singlet molecule is one in which the absorption of energy has shifted a valence electron from its normal bonding orbital to an antibonding orbital of higher energy, and in which the electron spins are paired (oxygen is an unusual diatomic molecule in that the spins of the two valence electrons of lowest energy are not paired in the most stable or ground state). The resultant excited molecule is highly unstable and must release its excess energy through different pathways or recombinations. Several studies have previously shown that artificially generated singlet oxygen reacts with regions of high electron density in microbial substrates.

For an ionized gas produced in an electrical discharge to be properly termed a plasma, it must satisfy the requirement that the concentrations of positive and negative charge carriers are approximately equal. This criteria is satisified when the dimensions of the discharged gas volume characterized by $\Lambda$ are significantly larger than the Debye length $$\lambda_O = (\xi_o kT_e/ne^2)^{\frac{1}{2}}$$

which defines the distance over which a charge imbalance can exist. In the above formula $\xi_o$ is the permittivity of free space, k is the Boltzmann constant, $T_e$ is the electron temperature, n is the electron density, and e is the charge on the electron. The plasma referred to in the present invention are glow discharges plasma and they are also called low temperature gas plasma. This type of plasma is characterized by average electron energies of 1–10 eV and electron densities of $10^9$ to $10^{12}$ per $cm^3$. Contrary to the conditions found in arcs or plasma jets, the electron and gas temperatures are very different due to the lack of thermal equilibrium. In other words, in a glow discharge, the electron temperature can be ten to a hundred times higher than the gas temperature. One can, therefore, use this invention to kill spores or microorganisms which contaminate the surfaces of thermally sensitive materials. In a low temperature gas plasma one can roughly distinguish two types of reactive elements: those which consist of atoms, ions or free radicals and those which pertain to small high energy particles such as electrons and photons. In glow discharges a large amount of ultraviolet radiation is always present. The UV high energy photons (3.3 to 6.2 ev) will produce strong cidal effects because they correspond to a maximum of absorption by DNA (deoxyribonucleic acid) and other nucleic acids. However, in the case of spores which can reach one millimeter in diameter, photon energy could be quickly dissipated through the various spore layers and this may restrict photochemical reactions to outer coats. UV photon energy from plasma, for instance, has been shown to be responsible (G. Kujirai et al, 1968) for surface cross-linking of polyethylene. The depth of action is, however, restricted to a one micro layer. The maximum observed depth for photochemical action in non-oxygen plasma was 10 microns in the case of polyethylene gelation or ablation. In other words, the photon energy is rather restricted to thin layer surface modifications (changes in plastics wettability and bondability) and will, therefore, be more efficacious when dealing with the smaller non-sporulated bacteria. In the case of high resistance spores, the photonic action may contribute to partial alteration of the disulphide rich proteins coat and thus facilitate the diffusion of free radicals, atoms, or excited molecules inside the core region. It has long been suspected (U.S. Pat. No. 3,968,248) that the cidal action of aldehydes is due to their alkylating properties. It is speculated that the aldehydes act through blockage and reaction with the sulfhydryl, hydroxyl, amino and carboxy groups present in spore cell proteins. The size of the aldehyde monomer molecules has also been regarded (Boucher, 1973) as a critical factor in cidal efficacy. The smaller formaldehyde, glyoxal and glutaraldehyde molecules are more lethal to spores than adipaldehyde, or heptanedial. It is also well-known (C. R. Phillips, 1965) that formaldehyde gas is far more sporicidal than the corresponding aqueous solutions of this chemical. The more recent theoretical concepts (Boucher, 1974) stressed the fact that the sporicidal activity seems always linked, other things being equal, to the content of free aldehyde monomers. The present invention shows that small amounts of vaporized aldehyde monomers and free radicals present in a low temperature gas plasma can greatly increase the overall biocidal action of a gas plasma.

Let us now consider a few mechanisms which can explain the enhanced sporicidal activity observed in aldehydes seeded low temperature plasma. Due to the presence of atomic or excited oxygen in the gas phase, the aldehydes can produce short life very reactive epoxides which can interact with may proteins and nucleic acids groups (amino, imino, hydroxyl, mercapto, etc.) in outer layer coats. In the case of glutaraldehyde, for instance, one can speculate that the commercial formulation always contains a certain amount of $\alpha,\beta$ unsaturated aldehydes due to aldol condensation. This would, for instance, lead to an epoxide according to the following schematic:

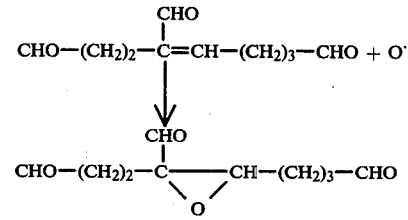

It is interesting to recall that such an aldehyde-epoxide has been detected (Peracchia and Mittler, 1972) in liquid phase after peroxide addition. It was also reported that it penetrated tissues faster during fixation. The same type of rapid interaction with outer layer proteins could, therefore, be expected from an epoxide created in an oxidizing plasma.

If one now considers the case of formaldehyde, the following photolysis (Calvert and Pitts, 1966) reactions take place in the low temperature gas plasma:

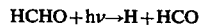

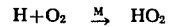

One has also recently observed (J. J. Bufalini et al, 1972) the following reaction:

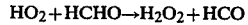

As previously demonstrated (R. Trujillo, 1972), the sporicidal activity of formaldehyde seems directly related to the concentration of free aldehyde radicals from the monomer. Among other theoretical possibilities to increase sporicidal action, one should also recall the potential oxydation of formaldehydes gas into formic acid HCOOH through photolysis. Formic acid as a vapor was shown to be (S. Kaye, 1968) a potent pretreatment agent to increase the sporicidal efficacy of epoxides. In the case of formaldehyde, there is, therefore, a very favorable set of conditions to attack the spore outer layers with active oxygen and facilitate several types of reactions with proteins amine groups while also increasing the penetration and density of aldehyde radicals in the critical areas of the spore. In short, a low temperature oxidizing gas plasma seeded with aldehydes will provide numerous reactive intermediates and free radicals to alter the spore outer coats and thus improved the diffusion of cidal groups.

The next possible step in the diffusion of cidal groups is the penetration inside the cortex layer whose major component is the polymer murein (or peptidoglycan). Murein is a large, crosslinked, net-like molecule exhibiting several unusual features. For instance, it contains an amino-sugar, muramic acid, which is not found in higher organisms, and also several amino acids in the unusual D-configuration as well as rare $\gamma$ glutamyl peptide bonds (in contrast to the $\alpha$ peptide bond of proteins). Under photonic UV irradiation consider what may happen to the polymer like cortex layer. Polymer-oxydation will take place due to the reactions with atomic oxygen (H. R. Hanson et al, 1965):

$$O_2 \rightarrow O^{\bullet} + O^{\bullet}$$

$$RH + O^{\bullet} \rightarrow R^{\bullet} + R\,O^{\bullet} \text{ or } R^{\bullet} + OH^{\bullet}$$

$$R^{\bullet} + O^{\bullet} \rightarrow RO^{\bullet}$$

$$R^{\bullet} + O_2 \rightarrow ROO^{\bullet}$$

The amino sugar molecule will be quickly oxidized since it is known from Hozumi and Matsumoto (1972) studies that for sucrose in gas plasma there is a quasi linear dependence of the oxidation rate up to 30 watts. For instance, the weight loss of a sucrose sample of 150 mg. can reach 42 mg/hr. in a 14 MHz oxidizing plasma with a power output of 20 watts (pressure 1 mm. Hg.). Besides mere oxydation, the amine groups from both the muramic acid molecule and the mucopeptide may react with the aldehydes. Hughes and Thurman (1970) proposed, for instance, that di-aldehydes could join together 2 contiguous side chains in *B. subtilis* mucopeptide in the case where both tripeptides carry free $\epsilon$-amino groups. A conjugated attack by atomic oxygen and aldehyde radicals will, therefore, quickly shake and modify in many ways the tight polymer structure of the cortex layer. This enhanced destruction of the cortex due to the addition of activated radicals has already been observed (U.S. Pat. No. 3,701,628) with chlorine, iodine, and bromine in ionized form. In this case, it has been speculated that the superoxide anion radicals (hypohalite anions $OI^-$, $OCL^-$, and $OBr^-$) are the microbiocidal agents.

Another interesting possibility is the potential alteration of the hypothetical pathway of dipicolinic acid synthesis (Kanie et al, 1966) by the aldehydes. It has long been speculated that since calcium and dipicolinic acid (DPA) occur in spores in roughly equimolar amounts, they form a salt complex whose role is capital in spores resistance. The exact location of the calcium salt in spores is a problem which remains to be solved. However, it is known that Diaminopimelic acid (DAP), which is an intermediate in the production of dipicolinic acid, is invariably present in the cortex of dormant spores. The fast access of aldehydes into the cortex (mainly a result of gas plasma oxidation) could help blocking the amine groups of the aspartic $\beta$-semialdehyde thus interfering directly with the DPA synthesis.

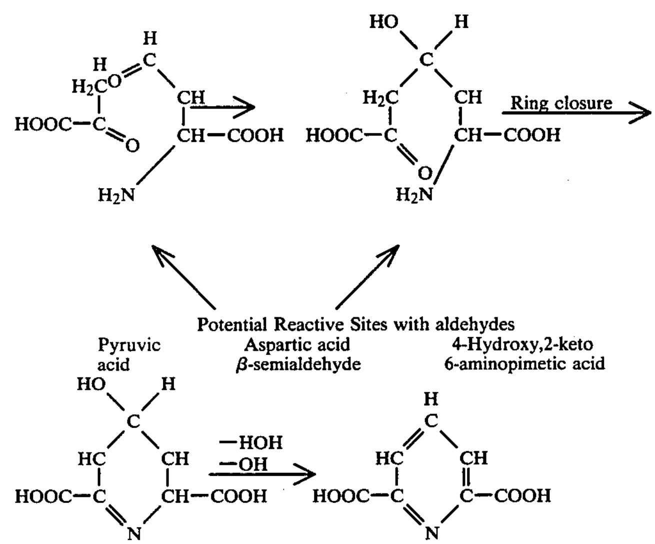

Potential Reactive Sites with aldehydes
Pyruvic acid
Aspartic acid β-semialdehyde
4-Hydroxy,2-keto 6-aminopimetic acid
4-Hydroxy,3,5-dihydroxy-Dipicolinic acid
Dipicolinic acid This mechanism could indeed explain why short exposures to a plasma gas in the presence of aldehydes can quickly destroy spores or their germinating capabilities. The aldehydes seeding method of the present invention essentially results in a shorter contact time in gas plasma to achieve a sporicidal effect and this indeed could be understood on the basis of the hypothesis hereabove underlined.

The cidal action of a low temperature aldehyde seeded gas plasma is so fast sometimes (less than ten minutes) that the possibility of inducing reactions inside the core or protoplst is rather small. The central portion of the spore is functionally a vegetative bud. It contains the hereditary charter, a repressed protein synthesizing system, the enzymes necessary to initiate the synthesis of new enzymes and structural materials, and, presumably, reserves for the supply of energy intermediates. There is little doubt that the modifications taking place in the outer coats cortex and plasma membranes are sufficient to fully explain the cidal results obtained with the present invention. When hereabove speaking of oxydation phenomena in a gas plasma, it is not restricted to the use of pure oxygen as an ionized gas but includes the use of oxygen-containing gases like air, $CO_2$ and $N_2O$. Although not as fast as oxydizing plasmas, the noble gas (argon, helium, etc.), and nitrogen plasmas, can be seeded with aldehydes to decrease sterilization time. In this case, the basic reactions taking place in a polymer structure are believed to be of the following type:

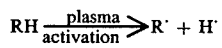

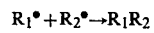

and they are often referred to as (R. H. Hansen et al, 1966) "cross-linking by activated species of inert gases."

One can say, therefore, that all other things being equal, the present invention enables reducing the spores killing time considerably over the values observed in standard oxidizing and non-oxidizing gas plasmas. While excited ions, gas molecules, and photons profoundly modify the protective layers of the spores, active aldehyde radicals flood the changing structures and initiate many additional lethal reactions which accelerate the killing process. A faster surface sterilization time means a more economical process and gives the possibility to handle many highly heat sensitive materials which could be degraded by prolonged exposure to the gas plasma even at temperatures below 100° C. Contrary to the seeding with halogen containing gases (U.S. Pat. No. 3,701,628), no severe corrosive or toxic residuals are observed when adding aldehydes to a gas plasma.

DESCRIPTION OF THE PREFERRED EMBODIMENTS

To produce a gas plasma of the type required in the present invention, one can, for instance, excite the carrier gas with two different radio-frequency methods. The first approach consists of a ring type or inductive discharge technique, while the second method consists of a parallel plate or capacitive discharge technique. The processing area consists always of a glass, plastic, or aluminum chamber under subatmospheric pressure (generally 0.1 to 10 mm. of mercury) into which a controlled flow of gas and aldehyde vapor is constantly moving under the continuous suction of a vacuum pump. To excite gases and vapors into the processing area, one couples the radio-frequency energy delivered by a generator through an inductive coil (wrapped around the processing chamber) or by means of capacitive discharge plates placed outside the chamber or chamber entrances. While in operation, the RF discharge glow can be made to extend virtually throughout the entire processing chamber. In a few cases the electrodes could even be positioned into the processing chamber.

There are indeed many ways to design electronic circuitry for maximizing RF energy coupling into the discharging gas. Descriptions of this kind of circuitry have been given in many papers, such as: *Anal. Chem.*, 34:1454, (1962); *Anal. Chem.*, 37:314 (1965) and the *Journal of Chemical Education*, Vol. 43, No. 6, A49-7–512, June (1966). In short, energy coupling optimization which can reach up to 90% is done by matching the gas load impedance to the impedance of the amplifier plate output circuit and the tank coil. The best impedance matching is achieved by a tuning process which consists of adjusting variable condensers in a low impedance matching network connected by coaxial cables between the reactor chamber and the generator. In more modern designs, the processing chamber and the relatively low power generator are coupled directly through high impedance connectors. This eliminates the complicated low impedance network and simplifies the electronic package. During power coupling to the gas plasma, a small amount of power is always lost due to heating effects. There is also an amount of power reflected back to the generator. To know how efficiently one is discharging energy in the gas, a RF wattmeter is often inserted in the electronic circuit to monitor the difference between forward and reflected power.

Regarding the radio-electric emission frequency, gas plasma generators operate generally around 13.5 Megahertz, but frequencies in the 1 to 30 Megahertz range would also be satisfactory. The method of the present invention could also be used at higher frequencies in an area known as the microwaves region. Frequencies would then range from 100 Megahertz to 300,000 Megahertz. A preferred frequency from the practical view point would then be 2450 Megahertz. While operating in the microwave region, it is interesting to recall that contrary to radio-frequencies, the atomic or excited molecular species have a longer life time and they can persist downstream quite a distance into the glowless region. This is an advantage from the analytical view point, but it is also balanced by the fact that microwave electronic circuitry is more complicated and, therefore, more expensive. When using microwave gas excitation, the processing chamber is designed as a cavity, the generator is generally a magnetron type device and the electro-magnetic energy is conveyed by standard wave guides.

No matter the gas excitation frequency, it has always been observed that the presence of small amounts of aldehyde vapors in the plasma considerably reduces the time needed to kill sporulated and non-sporulated bacteria.

These together with other objects and advantages which will become subsequently apparent reside in the details of construction and operation as more fully hereinafter described and claimed, reference being had to the accompanying drawings forming part hereof, wherein like reference numerals refer to like parts throughout.

FIGS. 3 and 3a represent a detailed view of a sterilizing tunnel; and

FIG. 4 is another embodiment showing the use of the microwave frequencies.

Figure 1:
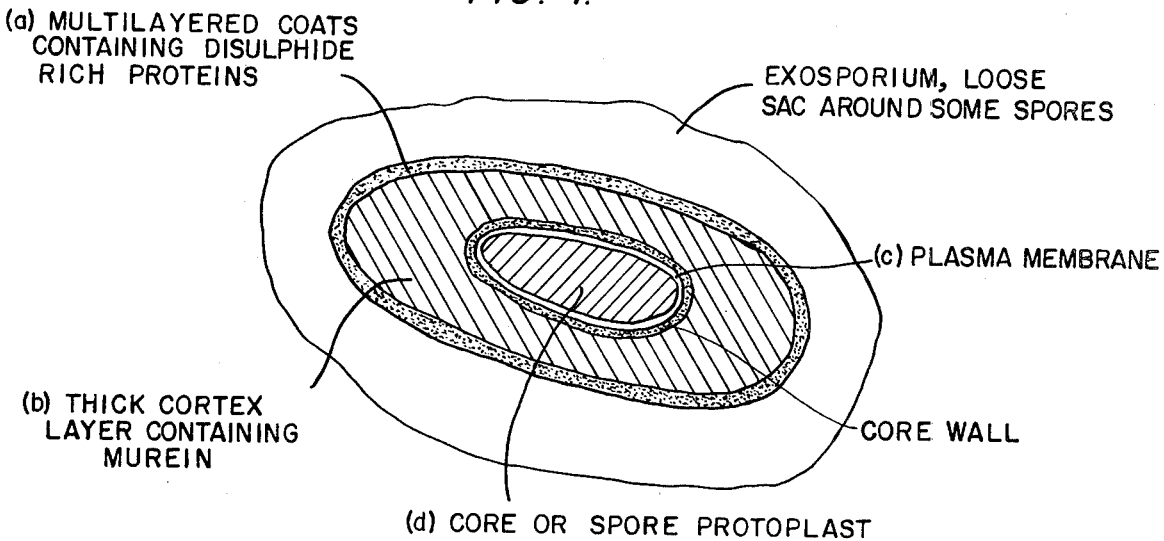
FIG. 1 represents the ultra typical structure of a typical bacterial spore.
Figure 2:
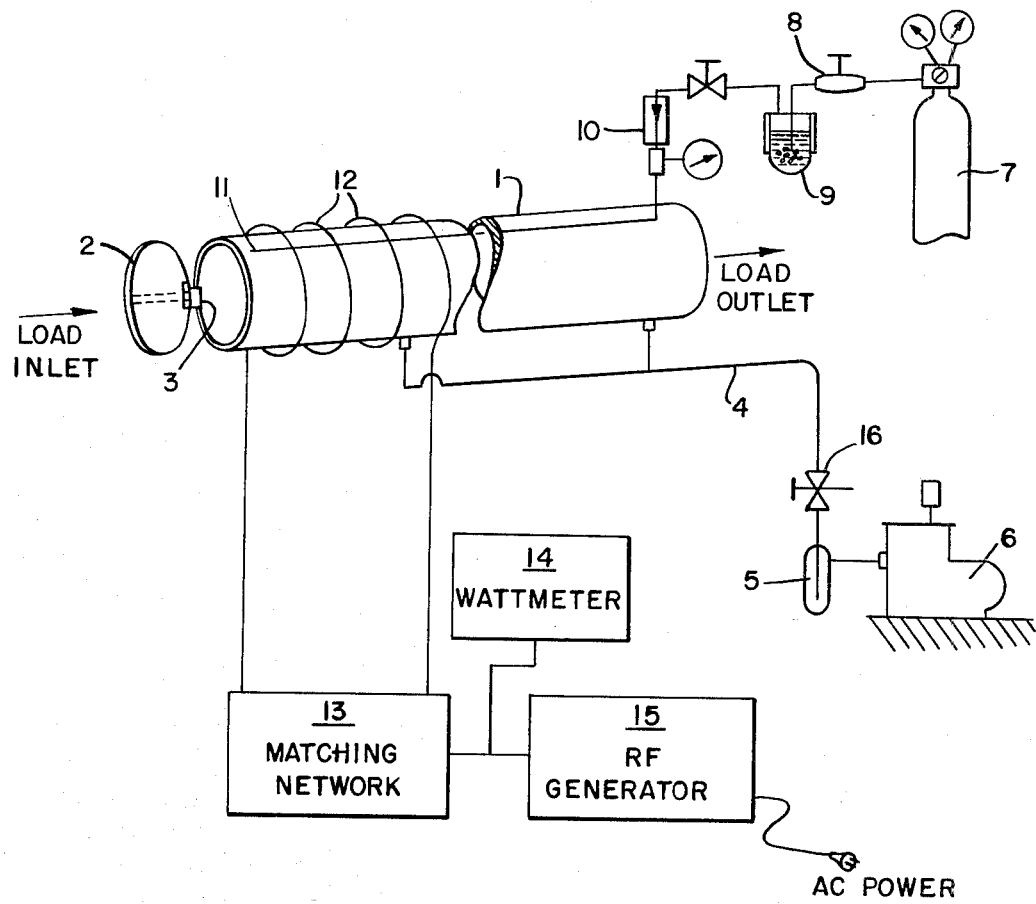
FIG. 2 represents system for sterilizing various hospital type disposals in a semi-continuous manner.

FIG. 2 shows the key components of a low temperature seeded plasma (referred to later as LTSP) system used for sterilizing in a semi-continuous manner various hospital type disposals. One can see that the system consists of a tunnel processing chamber 1, with a door 2 at both ends. For the sake of clarity, the second door on the exit right side is not shown. The disposables or non-disposables (for instance, plastic bottles of parenteral or ophtalmological solutions) are loaded in the cylindrical tunnel chamber by means of a standard automatic rail conveyor type system not shown. After loading, the front and rear door are shut down automatically by means of an electrically driven mechanical system 3. The loaded tunnel processing chamber is then submitted to subatmospheric pressure by means of a vacuum line system 4 connected to a trap 5 and to a vacuum pump 6. A vacuum of the order of 0.1 to 10 mm. of mercury is then established inside the entire processing chamber.

The gas to be ionized is delivered from a compressed gas line or bottle 7. Its pressure and flow rate are regulated by pressure gauges and by a constant flow rate membrane or needle value 8. Aldehyde vapors are added to the gas flow in a container 9 which allows the gas to bubble and entrain the vapors. A flowmeter 10 can be inserted between the aldehydes container and the inlet into the tunnel chamber. The mixture of gas and vapor is delivered through a hollow pipe line 11 with numerous small holes properly spaced for an even distribution into the tunnel chamber.

After evacuating most of the air in the tunnel chamber, the gas/vapor mixture is released in the processing area. The gas/aldehyde vapor flow is adjusted according to the size and volume of the tunnel. The plasma is then initiated by proper impedance matching with inductive and capacitive controls. In the system shown in FIG. 2, the plasma is induced by an RF coil 12 which is part of an electrical circuit comprising a matching network 13, a power wattmeter 14 and the RF generator 15 converting AC standard current into 13.56 MHz high frequency. The RF generator to be used for sustaining a plasma discharge must be capable of withstanding large variations in the load impedance. It essentially comprises a DC power supply, a crystal controlled RF oscillator and a solid state buffer amplifier. Final amplification is accomplished by a power amplifier designed around a power tube to accommodate large variations in load impedance. It is also important to recall that according to the type of installation one can either drive a single inductive coil (extending over the entire tunnel length) from a single power generator or operate series of smaller coil sections from smaller modular type RF generators.

After tunnel loading with contaminated equipment, the following sequences take place: Closure of end doors, air elimination through the vacuum line, introduction of the gas/aldehyde vapor, RF excitation, continuous removal of gas plasma flow during the necessary time period (between 5 and 20 minutes) to achieve complete sterilization. The RF excitation is then automatically shut down, the gas flow is interrupted and the vacuum pump is stopped. Air is introduced automatically in the tunnel chamber by the two-way valve 16. The two end doors are electro-mechanically opened and the samples container is automatically pulled out from the tunnel on a railing sliding system. The tunnel chamber is then ready for sterilizing a new load. The entire sterilization cycle time is generally comprised between 10 and 30 minutes according to the type of processed material and power output level.

FIGS. 3 and 3a are a more detailed view of a longitudinal and lateral cross section, respectively, of a sterilizing tunnel type processing chamber as shown in FIG. 2. The tunnel 17 is of cylindrical shape around the main axis. It essentially consists of two cylindrical pipes 18 and 19 made of highly resistant inert material such as glass or plastic (polysulfone, for instance) which are held by compression on end flanges with silicone type O rings 20. After assembling the internal pipe 19 inside the external pipe 18, one creates a hollow space ring 21 into which vacuum and subatmospheric pressure will be created by vacuum pump suction through bottom openings 22. To allow creating a subatmospheric atmosphere around the objects to be decontaminated, slots or holes 23 are perforated at the bottom of the internal cylinder 19. The objects to be sterilized (in our example plastic bottles 24 of parenteral solutions) are placed in a basket of parallelepipedic shape 25 which slides over a rail track 26 on roller bearing equipped wheels 27. At the beginning of the sterilizing cycle, the front and end doors 28 and 29 are automatically opened by an electrically operated device 30 which rotates the door 180° around the hinge 31. The front and end doors of the tunnel are generally made of a dark ultraviolet absorbing plastic material to stop the dangerous photon emission while allowing to see when the gas plasma glows at its maximum intensity. When the tunnel chamber operates at subatmospheric pressure, circular O rings 32 help producing a good seal with the doors. The mixture of reactive gas and aldehyde vapor is introduced in the processing tunnel through a small pipe 33 with perforated holes 34. The small pipe for gas and vapor introduction enters the tunnel at one end and is positioned in the upper part of the internal pipe 19 to allow uniform gas diffusion over the entire tunnel length. In FIG. 3, the RF inductive coil 35 is wrapped around the main external body of the processing tunnel 17.

FIG. 4 is another embodiment which allows practicing the present invention in the microwave frequencies range from 100 MHz to 300,000 MHz. The frontal cross section of the microwave gas plasma sterilizer shown in FIG. 4 derives directly from a piece of equipment previously described in U.S. Pat. No. 3,753,651. It essentially consists of a metal housing 35 quite similar to those used today in microwave ovens. Located within the housing are the main components of the low temperature microwave gas plasma system. They comprise the magnetron 36 which, with the help of the transformer, rectifier, and magnetic field circuit (all contained in power pack 37), converts the 60 cycles AC current from the main line 38 into microwave energy. The high power beam of microwave energy at 2450 MHz is contained in a wave guide 39 and directed against the blades 40 of a fan 41 which rotates at a slow RPM. The fan, often called "stirrer", reflects the power beam bouncing it off the walls, ceiling, back and bottom of the oven cavity 42. At the bottom of the oven cavity 42, one can see a pyrex glass plate 43 transparent to microwaves, which is suspended approximately one inch above the metal bottom of the processing cavity. The instruments or material to be surface sterilized 44 are placed inside a gas tight sealed container 45 which is positioned in the oven cavity 42 and rests upon the glass plate 43. The container 45 can be made of any material transparent to microwave energy: plastics (polypropylene, polyethylene, polystyrene, Teflon, etc.) carton board, paper or special glass composition. The container shown in FIG. 4 is of parallelepipedic shape with an upper lid 46 also made of microwave transparent material.

The lid has two openings 47 and 48 each with a stopcock or valve 49 and 50 to allow the introduction of the gas/aldehyde vapors mixture in the partial vacuum atmosphere comprised between 0.1 and 10 mm. of mercury. The container 45 contains two trays 51 which support the equipment (here plastic bottles 44 for ophtalomogical solutions) to be sterilized. The trays 51 are generally perforated to allow a more uniform diffusion of the ionized gas plasma. In the lower tray, a plastic cup 52 is inserted which contains the aldehyde solution 53 to be evaporated. Due to the thermal effect of microwaves, the aldehyde solution is gradually evaporated in the gas plasma when microwave energy is switched on. The carrier gas to be ionized is delivered from a gas bottle into a pressure line 54 which includes a constant flow valve 55 and a pressure gauge 56. One can also include, if needed, a flowmeter. The low pressure vacuum needed to empty the loaded container is created in the vacuum line 57 which is connected to a trap 58 and to the vacuum pump 59 shown on the left side of the housing 35.

A complete sterilizing cycle will correspond to the following sequence of operations: filling the trays with the equipment to be decontaminated, introduction of the aldehyde solution cup, air elimination by vacuum activation, introduction of the carrier gas, switching on microwaves during the necessary time period (between 5 and 20 minutes) to maintain a continuous plasma flow. At the end of the exposure time, there is an automatic shut down of the microwave generator, the carrier gas flow is also stopped and the vacuum is broken through the two way valve 60. The door of the microwave oven cavity is then opened and one can remove the container 45 after disconnecting the flexible tubings fastened to the stopcocks 49 and 50. The loaded container 45-6 can be kept sterile by the quick closing of the stopcocks 49 and 50 until there is a need to remove the decontaminated equipment under aseptic conditions. An entire sterilization cycle will generally last between 10 and 30 minutes. At no time during processing will the surface temperature approach or exceed 100° C. No de-aeration of the decontaminated equipment is needed since the oxidizing plasma does not leave detectable traces of chemical on the treated surfaces.

It is interesting to note that the semicontinuous sterilizing process shown in FIGS. 2, 3, 3a, and 4 can be adapted to deliver sterile instruments inside packages if the package is punctured by a small hole giving access to the ionized and excited gas mixture. At the end of the sterilization, the package can be removed under white room conditions and a small sterile tape will then cover and seal the small hole. The sealing tape can be fastened manually or by an automatic machine.

Having described our sterilization method and the sporicidal gaseous compositions to be used with it, we shall now give several examples to further illustrate the invention. They are given primarily for the purpose of illustration and should not be construed as limiting the invention to the details given.

EXAMPLES

Example No. 1

The experiments were conducted in a device as previously shown in FIG. 2. The carrier gases used as plasma were pure oxygen, argon, and nitrogen. The aldehyde vapors added to the carrer gas were produced in a bubbler with solutions of the following aldehydes: Formalin (8% formaldehyde) Acetaldehyde, Glyoxal, Malonaldehyde, Propionaldehyde, Succinaldehyde, Butyraldehyde, Glutaraldehyde, 2 Hydroxyadipaldehyde, Crotonaldehyde, Acrolein, and Benzaldehyde. The carrier gas flow rate was comprised between 80 cc. and 100 cc. per minute at room temperature. The emission frequency was 13.56 MHz and the average power density output in the plasma processing chamber was of the order of 0.015 watts per cubic centimeter. The minimum amount of aldehydes maintained in the continuous gas plasma flow was of the order of 10 mgrs. per liter. The sporicidal data presented in the examples was, in all instances, obtained according to the USDA approved fumigant sporicidal test method described in the Official Method of Analysis of the Association of Official Analytical Chemists (12th ed., Nov. 1975).

As recommended in the AOAC procedure, two types of highly resistant strains of the following species: *B. subtilis* (ATCC 19659) and *Cl. sporogenes* (ATCC 3584), were used in the experiments. The spores carriers were silk suture loops and porcelain cylinders which carried a dry spores load of $10^6$ to $10^9$ microorganisms. The spores carriers were individually suspended from a thin cotton thread attached to the gas pipe at the top of the processing chamber.

There was also added at the bottom of the processing chamber several spore test strips wrapped inside an ½ inch thick surgical gauze. These control spore strips (American Sterilizer Co. SPORDI®) were made of *Bacillus subtilis* (*globigii*) and *Bacillus stearothermophilus*. The subtilis strain was said to need a 60 minute exposure at 300° F. for complete kill in dry heat while it required one hour and forty-five minutes at 130° F. to be destroyed in the presence of ethylene oxide gas (conc. 600 mg. per liter, 50% RH). In all the experiments, the vacuum dried, acid resistant AOAC strains of *B. subtilis* and *Cl. sporogenes* proved to be far more resistant than the SPORDI® spores and, for the sake of simplicity, the results of the SPORDI® strips are not given in the data tables.

Table 1 shows the results of the experiments when trying to assess the influence of exposure time with the various low temperature aldehyde seeded plasmas. The controls consisted both of the gas alone (no aldehyde) and of a non-oxidizing plasma (hydrogen gas) with formaldehyde or glutaraldehyde vapors. For each type of sporulated bacteria on the specific carrier (loop or cylinder), ten samples were used. In the tables, the results are shown on a "pass" or "fail" basis respectively indicated by the letter "P", which denotes no growth in any of 10 samples, and "F", which denotes 1 to 10 samples having bacterial growth after proper culturing and heat shocking. For the sake of clarity, all "fail" tests which preceeded the first "pass" tests were omitted since it is obvious that shorter exposure times correspond to "fail" tests. As one can see, contact times between 10 and 30 minutes can provide satisfactory cidal action according to the type of aldehyde vapor utilized.

TABLE I

INFLUENCE OF EXPOSURE TIME IN L.T.S.P. (low temperature seeded plasma)

AOAC sporicidal test. (*B. subtilis* and *Cl. sporogenes* on Loops (L) and Cylinders (C). Gas flow rate: 80 cc. to 100 cc./min. Aldehydes flow rate: 10 mgrs./min. Electromagnetic power density: 0.015 watts per cc. of processing chamber. Electromagnetic frequency: 13.56 MHz. Average pressure in chamber: 0.5 mm. of mercury.

| CARRIER GASES: | | OXYGEN | | | | | | ARGON | | | | | | NITROGEN | | | | | |
|---|---|---|---|---|---|---|---|---|---|---|---|---|---|---|---|---|---|---|---|
| Exposure Time | | 10 | 15 | 30min. | 10 | 15 | 30min. | 10 | 15 | 30min. | 10 | 15 | 30min. | 10 | 15 | 30min. | 10 | 15 | 30min. |
| Type of Vaporised Aldehydes in Carrier Gas | Formula | *B. subtilis* LC LC LC | | | *Cl. sporogenes* LC LC LC | | | *B. subtilis* LC LC LC | | | *Cl. sporogenes* LC LC LC | | | *B. subtilis* LC LC LC | | | *Cl. sporo.* LC LC LC | | |
| Formaldehyde | HCHO | PP | | | PP | | | PP | | | PP | | | PP | | | PP | | |
| Acetaldehyde | CH$_3$—CHO | | PP | | | FP | PP | | PP | | | FP | PP | | FP | PP | | PP | PP |
| Glyoxal | OHC—CHO | PP | | | PP | | | PP | | | PP | | | PP | | | FP | PP | |
| Malonaldehyde | OHC—CH$_2$—CHO | | | PP | | | PP | | | PP | | | PP | | | PP | | | PP |
| Propionaldehyde | CH$_3$—CH$_2$—CHO | | PP | | | PP | | | PP | | | FP | PP | | PP | | | FP | PP |
| Succinaldehyde | OHC—(CH$_2$)$_2$—CHO | PP | | | FP | PP | | PP | | | FP | PP | | FP | PP | | FP | PP | |
| Butyraldehyde | CH$_3$—(CH$_2$)$_2$—CHO | | PP | | | PP | | | PP | | | PP | | | PP | | | FP | PP |
| Glutaraldehyde | OHC—(CH$_2$)$_3$—CHO | PP | | | PP | | | PP | | | FP | PP | | PP | | | FP | PP | |
| 2-Hydroxyadipaldehyde | OCH—(CH$_2$)$_3$—CH(OH)—CHO | | PP | | | PP | | | PP | | | PP | | | PP | | | PP | |
| Acrolein | H$_2$C=CH—CHO | PP | | | PP | | | PP | | | PP | | | PP | | | PP | | |
| Crotonaldehyde | H$_3$C—CH=CH—CHO | PP | | | | PP | | PP | | | | PP | | PP | | | | PP | |
| Benzaldehyde | C$_6$H$_5$—CHO | | PP | | | PP | | | PP | | | PP | | | PP | | | FP | |
| CONTROLS (Hydrogen-Formaldehyde) | | | FP | | | FF | | | FF | | | FF | | | FF | | | FF | |
| Carrier Gas Alone (no aldehyde) | | | PP | | | FP | | | PP | | | FP | | | FP | | | PP | |

Example No. 2

This test was conducted under the same experimental conditions as that of the first example, but the exposure time was maintained around 15 minutes while the power output was increased approximately from 0.001 watts per cm$^3$ of processing chamber to 0.015 and 0.1 watts per cm$^3$. As one can see from Table II data, no killing was achieved at the lowest power density, but excellent results were often obtained in the 0.015 to 0.1 watts per cm$^3$ range. Here again one can see the increased killing power due to the addition of aldehyde traces in the gas plasma. Oxygen appeared the best carrier among the gases used in this experiment. Here again for the sake of clarity, all "fail" tests which preceeded the first "pass" tests were omitted in the Table since it is obvious that lower power densities correspond to "fail" tests.

TABLE II

INFLUENCE OF POWER OUTPUT DENSITY IN L.T.S.P. (low temperature seeded plasma)

AOAC sporicidal test (*B. subtilis* and *Cl. sporogenes* on Loops (L) and cylinders (C)). Gas flow rate: 80 cc. to 100 cc./min. Aldehydes flow rate: 10 mgrs./min. Electromagnetic frequency: 13.56 MHz. Average pressure in the chamber: 0.5mm. of mercury. Exposure time: 15 min.

| CARRIER GASES | | OXYGEN | | | | | | ARGON | | | | | | NITROGEN | | | | | |
|---|---|---|---|---|---|---|---|---|---|---|---|---|---|---|---|---|---|---|---|
| Power Density in 10$^{-3}$ watts/cc. of chamber | | 1 | 15 | 100 | 1 | 15 | 100 | 1 | 15 | 100 | 1 | 15 | 100 | 1 | 15 | 100 | 1 | 15 | 100 |
| Type of vaporised aldehydes in carrier gas | Formula | *B. subtilis* LC LC LC | | | *Cl. sporogenes* LC LC LC | | | *B. subtilis* LC LC LC | | | *Cl. sporogenes* LC LC LC | | | *B. subtilis* LC LC LC | | | *Cl. sporogenes* LC LC LC | | |
| Formaldehyde | HCHO | | PP | | | PP | | | PP | | | PP | | | PP | | | PP | |
| Acetaldehyde | CH$_3$—CHO | | PP | | | FP | | | PP | | | FP | PP | | FP | PP | | FP | PP |
| Glyoxal | OHC—CHO | | PP | | | PP | | | PP | | | PP | | | PP | | | PP | |
| Malonaldehyde | OHC—CH$_2$—CHO | FF | PP | | FF | PP | | FF | PP | | FF | PP | | FF | PP | | FF | PP | |
| Propionaldehyde | CH$_3$—CH$_2$—CHO | | PP | | | PP | | | PP | | | FP | PP | | PP | | | FP | PP |
| Succinaldehyde | OHC—(CH$_2$)$_2$—CHO | | PP | | | PP | | | PP | | | PP | | | PP | | | PP | |
| Butyraldehyde | CH$_3$—(CH$_2$)$_2$—CHO | | PP | | | PP | | | PP | | | PP | | | PP | | | FP | PP |
| Glutaraldehyde | OHC—(CH$_2$)$_3$—CHO | | PP | | | PP | | | PP | | | PP | | | PP | | | PP | |

TABLE II-continued
INFLUENCE OF POWER OUTPUT DENSITY IN L.T.S.P. (low temperature seeded plasma)

AOAC sporicidal test (*B. subtilis* and *Cl. sporogenes* on Loops (L) and cylinders (C) ). Gas flow rate: 80 cc. to 100 cc./min. Aldehydes flow rate: 10 mgrs./min. Electromagnetic frequency: 13.56 MHz. Average pressure in the chamber: 0.5mm. of mercury. Exposure time: 15 min.

| CARRIER GASES | | OXYGEN | | | ARGON | | | NITROGEN | | |
|---|---|---|---|---|---|---|---|---|---|---|
| Power Density in $10^{-3}$ watts/cc. of chamber | | 1  15  100 | | | 1  15  100 | | | 1  15  100 | | |
| Type of vaporised aldehydes in carrier gas | Formula | *B. subtilis* LC LC LC | *Cl. sporogenes* LC LC LC | *B. subtilis* LC LC LC | *Cl. sporogenes* LC LC LC | *B. subtilis* LC LC LC | *Cl. sporogenes* LC LC LC | | | |
| 2-Hydroxy-adip-aldehyde | OHC—(CH$_2$)$_3$—CH—CHO<br>　　　　　　　　\|<br>　　　　　　　　OH | FF PP | FF PP | FF PP | FF PP | FF PP | FF FF | | | |
| adip-aldehyde Acrolein | H$_2$C=CH—CHO | PP | PP | PP | PP | PP | PP | | | |
| Croton-aldehyde | H$_3$C—CH=CH—CHO | PP | FF PP | PP | FF PP | PP | FF PP | | | |
| Benz-aldehyde | C$_6$H$_5$—CHO | FF PP | FF PP | FF PP | FF PP | FF PP | FF PP | | | |
| CONTROLS (Hydrogen-Formaldehyde) | | FP | FF | FF | FF | FF | FF | | | |
| Carrier Gas Alone (no aldehyde) | | FF PP | FP | FF PP | FF FP | FF FP | FF FP | | | |

Example No. 3

This test shows how important is the amount of aldehyde in the gas plasma. For this study, the aldehydes were vaporized from a 2% active ingredients solution and this corresponded roughly to a consumption of 15 cc. during a 15 minute run. However, when sampling the gas plasma, the concentration of aldehydes (formaldehyde, for instance) was found equal to 10 mgrs. per minute for a flow rate of 100 cc./min. This aldehyde concentration in the gas phase was roughly half the value to be expected from the vaporized aldehyde solution. It showed that approximately half the active aldehydes were deposited on the wall of the processing chamber. The concentrations given in Table III are those really observed in the gas plasma under normal operating conditions. At the lower level (0.1 mgrs./min.), no increase in sporicidal activity was observed with any of the three gases used in our test. At the 1 mgr./min. level, there was inconsistent results.

At the 10 mgrs./min. level, most of the aldehydes boosted the sporicidal efficacy of the gas plasma. At the 100 mgrs./min. level, all aldehydes showed an increased spores killing over what was observed with the aldehydes alone or with a non-oxidizing gas such as hydrogen loaded with aldehydes.

TABLE III
INFLUENCE OF THE AMOUNT OF VAPORISED ALDEHYDES IN L.T.S.P. (low temperature seeded plasma)

AOAC sporicidal test (*B. subtilis* and *Cl. sporogenes* on Loops(L) and cylinders(C)). Gas Flow rate: 80cc. to 100cc./min. Electromagnetic power density: 0.015 watts/cc. of chamber. Electromagnetic frequency: 13.56 MHz. Average pressure in the chamber: 0.5mm. of mercury. Exposure time: 15 min.

| CARRIER GASES | | OXYGEN | | ARGON | | NITROGEN | |
|---|---|---|---|---|---|---|---|
| Vaporised Aldehydes Flow Rate in mgrs/min. | | .1  10  100 | | .1  10  100 | | .1  10  100 | |
| Type of Aldehydes in carrier gas | Formula | *B. subtilis* LC LC LC | *Cl. sporogenes* LC LC LC | *B. subtilis* LC LC LC | *Cl. sporogenes* LC LC LC | *B. subtilis* LC LC LC | *Cl. sporogenes* LC LC LC |
| Formaldehyde | HCHO | PP | PP | PP | PP | PP | PP |
| Acetaldehyde | CH$_3$—CHO | PP | FP | PP | FP PP | FP PP | FP PP |
| Glyoxal | OHC—CHO | PP | PP | PP | PP | PP | PP |
| Malonaldehyde | OHC—CH$_2$—CHO | FF PP | FF PP | FF PP | FF PP | FF PP | FF PP |
| Propionaldehyde | CH$_3$—CH$_2$—CHO | PP | PP | PP | FP PP | PP | FP PP |
| Succinaldehyde | OHC—(CH$_2$)$_2$—CHO | PP | PP | PP | PP | PP | PP |
| Butyraldehyde | CH$_3$—(CH$_2$)$_2$—CHO | PP | PP | PP | PP | PP | FP PP |
| Glutaraldehyde | OHC—(CH$_2$)$_3$—CHO | PP | PP | PP | PP | PP | PP |
| 2-Hydroxy-adip-aldehyde | OCH—CH$_2$)$_3$—CH—CHO<br>　　　　　　　　\|<br>　　　　　　　　OH | FF PP | FF PP | FF PP | FF PP | FF PP | FF PP |
| Acrolein | H$_2$C=CH—CHO | PP | PP | PP | PP | PP | PP |
| Crotonaldehyde | H$_3$C—CH=CH—CHO | PP | FF PP | PP | FF PP | PP | FF PP |
| Benzaldehyde | C$_6$H$_5$—CHO | FF PP | FF PP | FF PP | FF PP | FF PP | FF PP |

TABLE III-continued
INFLUENCE OF THE AMOUNT OF VAPORISED ALDEHYDES IN L.T.S.P. (low temperature seeded plasma)

AOAC sporicidal test (*B. subtilis* and *Cl. sporogenes* on Loops(L) and cylinders(C)). Gas Flow rate: 80cc. to 100cc./min. Electromagnetic power density: 0.015 watts/cc. of chamber. Electromagnetic frequency: 13.56 MHz. Average pressure in the chamber: 0.5mm. of mercury. Exposure time: 15 min.

| CARRIER GASES | OXYGEN | | | | | | ARGON | | | | | | NITROGEN | | | | | |
|---|---|---|---|---|---|---|---|---|---|---|---|---|---|---|---|---|---|---|
| Vaporised Aldehydes Flow Rate in mgrs/min. | .1 | 10 | 100 | .1 | 10 | 100 | .1 | 10 | 100 | .1 | 10 | 100 | .1 | 10 | 100 | .1 | 10 | 100 |
| Type of Aldehydes in carrier gas Formula | *B. subtilis* LC LC LC | | | *Cl. sporogenes* LC LC LC | | | *B. subtilis* LC LC LC | | | *Cl. sporogenes* LC LC LC | | | *B. subtilis* LC LC LC | | | *Cl. sporogenes* LC LC LC | | |
| CONTROLS (Hydrogen-Glutaraldehyde) | FF | | | FF | | | FF | | | FF | | | FF | | | FF | | |
| Carrier Gas Alone (no aldehyde) | FF | | | FF | | | FF | | | FF | | | FF | | | FF | | |

Example No. 4

Table IV shows the results observed when replacing a single aldehyde composition by a mixture of two different aldehydes or by a mixed formula containing an aldehyde with a non-aldehyde compound (phenol). It can be seen that a mixed composition gives the same results as a single aldehyde solution as long as the total content in aldehydes remains the same in the two formulas. As theoretically expected, the presence of a phenol did not affect the aldehyde efficacy as a sporicidal booster agent in the gas plasma. It is indeed well-known (Techniques and Applications of Plasma Chemistry, J. R. Hollahan, page 103, John Wiley & Sons Ed., 1974) that due to their great bond strength, fluorine, the phenyl group and condensed aromatic systems are fairly inert in gas plasma. Here again the lower cidal efficacy of gas plasma without aldehydes has been confirmed under these experimental conditions.

Also not reported on Table IV were many experiments conducted with various solutions of germicidal agents other than phenols. While maintaining the same concentration of aldehydes, there was added the following ingredients in equal concentration: halogen compounds such as chloroisocyanurates (trichloro-S-triazinetrione) and iodophors (PVP-iodine complex); inorganic salts (selenium sulfide); an alcoholic solution of zinc undecylenate; ammonium quaternaries such as cetylpyridinium chloride; organo sulfurs such as methylenebisthiocyanate and nitrogen compounds of fatty amines type such as N-alkyl trimethylene diamine. In no case was there detected a synergistic effect due to the presence of these agents in the vapor phase. There was noted, however, a slight increase in activity (additive effects) each time the plasma vaporization led to the dissociation of the chemical salt with a release of a halogen. This additive cidal effect was indeed expected from the information given in U.S. Pat. No. 3,701,628. The strong corrosive effect of ionized halogens was also observed and this, as previously stressed, would make impractical the use of such chemicals in a seeded low temperature plasma gas.

TABLE IV
EFFICACY OF ALDEHYDES MIXTURE IN L.T.S.P. (low temperature seeded plasma)

AOAC sporicidal test (*B. subtilis* and *Cl. sporogenes*) on Loops (L) and Cylinders (C) Gas flow rate: 80 cc. to 100 cc/min. Electromagnetic power density: 0.015 watts/cc. of chamber. Aldehydes flow rate: 100 mgrs/min. Electromagnetic frequency: 13.56 MHz. Average pressure in the chamber: 0.5mm. of mercury. Exposure time: 15 min.

| CARRIER GASES | OXYGEN | | | | ARGON | | | | NITROGEN | | | |
|---|---|---|---|---|---|---|---|---|---|---|---|---|
| Type of aldehydes mixture (2% total content in aldehydes | *B.subtilis* L | C | *Cl.sporogenes* L | C | *B.subtilis* L | C | *Cl.sporogenes* L | C | *B.subtilis* L | C | *Cl.sporogenes* L | C |
| Formaldehyde + Glutaraldehyde | P | P | P | P | P | P | P | P | P | P | P | P |
| Succinaldehyde + Formaldehyde | P | P | P | P | P | P | P | P | P | P | P | P |
| Glutaraldehyde + Phenol | P | P | P | P | P | P | P | P | P | P | P | P |
| Butyraldehyde + Glutaraldehyde | P | P | P | P | P | P | P | P | P | P | P | P |
| Formaldehyde + Acetaldehyde | P | P | P | P | P | P | P | P | P | P | P | P |
| CONTROLS Carrier Gas Alone (no aldehydes) | F | F | F | F | F | F | F | F | F | F | F | F |

Example No. 5

The results of another type of experiment conducted in the microwave region are given in Table V. This test was conducted in the apparatus whose front cross section was shown in FIG. 4. Since it was operated at higher frequencies, the microwave glow discharge was more uniform inside the experimental polysulfone container. The gas plasma pressure (2 mm. of mercury) was slightly higher than in previous tests because microwave discharges are more difficult to initiate and to sustain at low pressures ($\leq 1$ mm. of mercury) than DC or RF discharges.

Due to the higher longevity and efficacy of free radicals and ionized species in a microwave gas plasma, the contact time was reduced to 10 minutes. The plastic-polysulfone container transparent to microwaves had the following dimensions: 6"×14"×12" (volume 16,37 liters). The average density of the electromagnetic energy inside the resonant cavity was tuned at the FCC authorized nominal frequency of 2540 MHz (±25 MHz). The gas flow rate was adjusted between 900 cc. and 1000 cc. per minute which corresponded to an average aldehyde content of 18 mgrs./min. in the plasma phase. During the 10 minutes processing around 18 cc. of each aldehyde solution (2% concentration by weight) was evaporated. This corresponded also to roughly twice the amount really present (9 cc.) for reaction in the gas plasma.

One can clearly see in Table V the increase in sporicidal efficacy due to the seeding of the small amount of aromatic, heterocyclic, saturated or unsaturated aldehydes in the electromagnetic continuous gas plasma discharge. When vaporizing furfural (2-Furaldehyde), the concentration of this chemical in the oxygen flow stream was 0.0018%. It is important to recall that with this chemical the lower explosive limit in air is 2.1% by volume. The 2% aqueous solution was maintained at all times during evaporation below the open cup flash point of this aldehyde which is around 68° C.

In the case of aromatic aldehydes (Benzaldehyde, for instance), several complex reactions may take place in the gas plasma and several activated species may play a role to combine with the previously mentioned key components of spore layers which affect its metabolism. In the case of Benzaldehyde, H. Suhr et al (1970) have, for instance, demonstrated the presence of the following intermediates under low electron energies and fast gas flow:

$$\text{C}_6\text{H}_5-\text{C}(=\text{O})\text{H} \rightarrow \text{C}_6\text{H}_5-\text{CO} \rightarrow \text{C}_6\text{H}_5 \cdot \xrightarrow{+H} \text{C}_6\text{H}_6$$

It is indeed speculative at this stage to pinpoint the particular species which would be responsible for interaction with the spores key components, however, it has been established that the presence of an aldehyde group is necessary to observe the results of the present invention. Besides Benzaldehyde, Thiophenaldehyde, and Pyridine-2-aldehyde have qualitatively shown the same behavior.

for instance, by capacitive plates; magnetrons replaced by Klystrons or amplitron tubes).

Having thus described the method of the invention in terms of their preferred embodiments as set forth in the description and the examples of the aforesaid specification, it is apparent to those skilled in the art that various changes and modifications can be made in the method without departing from the scope of the invention.

What is claimed is:

1. A method of sterilizing a surface comprising contacting said surface with a low temperature gas plasma containing at least 10 mg/l of an aldehyde under subatmospheric pressure.

2. A method in accordance with claim 1 wherein the aldehyde is at least one member selected from the group consisting of aromatic, heterocyclic and saturated and unsaturated acyclic aldehydes.

3. A method in accordance with claim 1 wherein said gas plasma is produced from electromagnetic excitation of at least one gas selected from the group consisting of oxygen, argon, helium, nitrogen, carbon dioxide and nitrogen oxide.

4. A method in accordance with claim 1 wherein the pressure of said gas plasma is equal to or greater than 0.1 mm. of mercury.

5. A method in accordance with claim 1 wherein said gas plasma is produced by gaseous electromagnetic discharges in the 1 to 100 MHz radio frequency region.

6. A method in accordance with claim 1 wherein said gas plasma is produced by gaseous electromagnetic discharges in the 100 to 300,000 MHz microwave range.

TABLE V

INFLUENCE OF SEEDED ALDEHYDES IN A L.T.S.P. (low temperature seeded plasma)
AOAC sporicidal test B.subtilis and Cl. sporogenes on Loops (L) and Cylinders (C)). Gas flow rate: 910cc. to 1000cc/min. Electromagnetic power density: 0.02 watts/cc. of chamber. Aldehydes flow rate in gas 9 mgrs./min. Electromagnetic frequency: 2540 MHz. Average pressure in the chamber: 2mm. of mercury. Exposure time: 10 min.

| CARRIER GASES | | OXYGEN | | ARGON | | NITROGEN | |
|---|---|---|---|---|---|---|---|
| Type of Vaporized Aldehydes in carrier gas | Formula | B.subtilis LC | Cl.sporogenes LC | B.subtilis LC | Cl.sporogenes LC | B.subtilis LC | Cl.sporogenes LC |
| Formaldehyde | HCHO | PP | PP | PP | PP | PP | PP |
| Acetaldehyde | $CH_3-CHO$ | PP | PP | PP | PP | PP | PP |
| Glyoxal | OHC—CHO | PP | PP | PP | PP | PP | PP |
| Malonaldehyde | $OHC-CH_2-CHO$ | PP | PP | PP | PP | PP | PP |
| Propionaldehyde | $CH_3-CH_2-CHO$ | PP | PP | PP | PP | PP | PP |
| Succinaldehyde | $OHC-(CH_2)_2-CHO$ | PP | PP | PP | PP | PP | PP |
| Butyraldehyde | $CH_3-(CH_2)_2-CHO$ | PP | PP | PP | PP | PP | PP |
| Glutaraldehyde | $OHC-(CH_2)_3-CHO$ | PP | PP | PP | PP | PP | PP |
| 2-Hydroxyadipaldehyde | $OHC-(CH_2)_3-CH(OH)-CHO$ | PP | PP | PP | PP | PP | PP |
| Acrolein | $H_2C=CH-CHO$ | PP | PP | PP | PP | PP | PP |
| Crotonaldehyde | $H_3C-CH=CH-CHO$ | PP | PP | PP | PP | PP | PP |
| Benzaldehyde | $C_6H_5-CHO$ | PP | PP | PP | PP | PP | PP |
| 2-Furaldehyde | $C_5H_4O_2$ | PP | PP | PP | PP | PP | PP |
| CONTROLS Carrier Gas Alone (no aldehydes) | | FP | FF | FP | FF | FF | FF |

In accordance with the above, it must be well understood that, according to the desired results, the present invention can be applied to variable flow rates of different gases at different temperatures or multiple pressures, and that, still without departing from the scope of the invention, the structural details of the described apparatuses, the dimensions and shapes of their members (such as tunnel or cavity sizes) and their arrangements (introducing aldehyde vapors in microwave field through evaporation or by a bubbler in the carrier gas line) may be modified, and that certain members may be replaced by other equivalent means (inductive RF coils replaced, 7. A method in accordance with claim 1 wherein said gas plasma is confined inside a fluid-tight container or chamber into which the electromagnetic field density is at least equal to 0.001 watts per cubic centimeter of space.

8. A method in accordance with claim 1 wherein said gas plasma contains at least one aldehyde selected from the group consisting of formaldehyde, acetaldehyde, glyoxal, malonaldehyde, propionaldehyde, succinaldehyde, butyraldehyde, glutaraldehyde, 2-hydroxyadipaldehyde, acrolein, crotonaldehyde, benzaldehyde, and 2-furaldehyde.

9. A method in accordance with claim 1 wherein the aldehyde vapors are introduced in a continuously produced gas plasma upstream in a carrier gas flow.

10. A method in accordance with claim 1 wherein the aldehyde vapors are introduced in a continuously produced gas plasma inside a plasma processing chamber.

11. A method in accordance with claim 1 wherein said gas plasma will also contain in an amount equal to or greater than ten milligrams per liter of said gas plasma of at least one vaporized biocidal agent selected from the group consisting of phenols, halogens, inorganic and organic metallic salts, organosulfur and nitrogen compounds.

12. A method of sterilizing surfaces, comprising:
 (a) placing the surface to be sterilized in a fluid-tight chamber;
 (b) evacuating said chamber to a pressure equal to or greater than 0.1 mm. of mercury;
 (c) introducing into the evacuated chamber a gas containing at least ten milligrams per liter of at least one vaporized aldehyde selected from the group consisting of aromatic, heterocyclic and saturated and unsaturated acyclic aldehydes per liter of gas plasma;
 (d) establishing an electromagnetic field in the 1 to 10,000 MHz range with an average spatial density of energy of at least 0.001 watts per cubic centimeter of chamber;
 (e) maintaining the abovementioned electromagnetic field for a time long enough to completely destroy all living microorganisms while not affecting the physical or chemical properties of the object to be decontaminated.

* * * * *